United States Patent
Minke et al.

(10) Patent No.: US 11,731,940 B2
(45) Date of Patent: Aug. 22, 2023

(54) PROCESS FOR PREPARING TRIACETONAMINE

(71) Applicant: Evonik Operations GmbH, Essen (DE)

(72) Inventors: Katharina Minke, Essen (DE); Holger Graskamp, Marl (DE)

(73) Assignee: Evonik Operations GmbH, Essen (DE)

(*) Notice: Subject to any disclaimer, the term of this patent is extended or adjusted under 35 U.S.C. 154(b) by 40 days.

(21) Appl. No.: 17/238,715

(22) Filed: Apr. 23, 2021

(65) Prior Publication Data

US 2021/0347733 A1    Nov. 11, 2021

(30) Foreign Application Priority Data

May 7, 2020   (EP) .................................... 20173463

(51) Int. Cl.
   *C07D 211/74*   (2006.01)
(52) U.S. Cl.
   CPC .................................. *C07D 211/74* (2013.01)
(58) Field of Classification Search
   CPC ................................................... C07D 211/74
   See application file for complete search history.

(56) References Cited

U.S. PATENT DOCUMENTS

| | | | |
|---|---|---|---|
| 2,351,352 A | 6/1944 | McAllister et al. | |
| 3,943,139 A | 3/1976 | Orban et al. | |
| 3,960,875 A | 6/1976 | Orban et al. | |
| 4,275,211 A | 6/1981 | Orban et al. | |
| 4,536,581 A * | 8/1985 | Cantatore ............ | C07D 211/02 546/242 |
| 4,831,146 A | 5/1989 | Taylor et al. | |
| 5,773,622 A | 6/1998 | Jegelka et al. | |
| 8,093,438 B2 | 1/2012 | Dimmit et al. | |
| 10,358,420 B2 | 7/2019 | Minke et al. | |
| 2018/0009752 A1 | 1/2018 | Minke et al. | |

FOREIGN PATENT DOCUMENTS

| | | |
|---|---|---|
| CA | 666225 | 7/1963 |
| CA | 668290 | 8/1963 |
| CA | 677298 | 12/1963 |
| CA | 722240 | 11/1965 |
| CA | 772201 | 11/1967 |
| CN | 102516158 | 6/2012 |
| CN | 103663773 | 3/2014 |
| CN | 103664745 | 3/2014 |
| CN | 103224465 | 4/2015 |
| CN | 105820108 | 8/2016 |
| CN | 105820109 | 8/2016 |
| CN | 106866503 | 6/2017 |
| CN | 107033066 | 8/2017 |
| CN | 108383704 | 8/2018 |
| DE | 2352127 | 4/1974 |
| DE | 24 29 936 | 1/1975 |
| DE | 2429935 | 1/1975 |
| DE | 2429937 | 1/1975 |
| DE | 28 07 172 | 8/1979 |
| DE | 31 35 489 | 3/1983 |
| DE | 10 2010 062 804 | 7/2011 |
| DE | 102012215903 | 3/2014 |
| DE | 10 2016 212 378 | 1/2018 |
| DE | 10 2016 212 379 | 1/2018 |
| EP | 0 004 104 | 9/1979 |
| EP | 0013865 | 8/1980 |
| EP | 0 033 529 | 8/1981 |
| EP | 0 776 887 | 6/1997 |
| EP | 2706056 | 3/2014 |
| EP | 3 255 039 | 12/2017 |
| EP | 3 663 284 | 6/2020 |
| EP | 3 750 876 | 12/2020 |
| JP | S54-88275 | 7/1979 |
| JP | S54-112873 | 9/1979 |
| JP | H04-154762 | 5/1992 |
| JP | H05-140104 | 6/1993 |
| JP | 2000-239257 | 9/2000 |
| JP | 2001-31651 | 2/2001 |
| JP | 2003-160561 | 6/2003 |
| JP | 2003-206277 | 7/2003 |
| JP | 2003-252858 | 9/2003 |
| JP | 2014-51493 | 3/2014 |

(Continued)

OTHER PUBLICATIONS

Extended European Search Report received for European Patent Application No. 20173463.9, dated Sep. 15, 2020, 14 pages including English Translation.

(Continued)

*Primary Examiner* — Timothy R Rozof

(74) *Attorney, Agent, or Firm* — Grüneberg and Myers, PLLC

(57) ABSTRACT

An improved process can be used for preparing triacetonamine. The process involves performing an absorption step in which acetone present in the crude product is removed from triacetonamine by distillation, and in gaseous form is then absorbed in countercurrent into fresh, liquid acetone. The acetone stream thus obtained is then converted further to triacetonamine. This process enables more energy-efficient reutilization of the unreacted reactants used in the synthesis of triacetonamine, and thus lowers overall both the use of reactants and the energy expenditure.

19 Claims, No Drawings

(56) References Cited

FOREIGN PATENT DOCUMENTS

RO              96131      1/1989
TW         201431839      8/2014
WO       2020/108980      6/2020

OTHER PUBLICATIONS

Translation of Taiwanese IPO Search Report dated Apr. 15, 2022 in Taiwanese Application No. 110116010, 1 page.
The Chemical Society of Japan, Kagaku Binran [Handbook of Chemistry], Applied Chemistry $7^{th}$ Edition, 2014, pp. 270-271 with partial translation.
Kirchhoff, et al., "Triacetoneamine Derivative:—Industrial Applications and Recent Developments", Polymers & Polymer Composites, vol. 8, 2000, pp. 245-254.

* cited by examiner

PROCESS FOR PREPARING TRIACETONAMINE

CROSS-REFERENCE TO RELATED APPLICATIONS

This application claims priority to European Patent Application No. 20173463.9, filed May 7, 2020, incorporated herein by reference.

BACKGROUND OF THE INVENTION

Field of the Invention

The present invention relates to an improved process for preparing triacetonamine. The process involves performing an absorption step in which acetone present in the crude product is removed from triacetonamine by distillation and in gaseous form is then absorbed in countercurrent into fresh, liquid acetone. The acetone stream thus obtained is then converted further to triacetonamine. This process enables more energy-efficient reutilization of the unreacted reactants used in the synthesis of triacetonamine and thus lowers overall both the use of reactants and the energy expenditure.

DESCRIPTION OF RELATED ART

Triacetonamine (2,2,6,6-tetramethyl-4-piperidinone; CAS number: 826-36-8; hereinafter "TAA") is an important chemical intermediate which is used for the synthesis of numerous derivative products, for example light stabilizers (hindered amine light stabilizers: [HALS]), oxidizing agents and polymerization moderators (e.g. nitroxyl radicals).

The preparation of triacetonamine from acetone and ammonia has been documented in the form of various processes. This includes the preparation processes of direct (single-step) synthesis of TAA from the reactants, for example described in DE 24 29 937 A1, U.S. Pat. No. 4,536,581 A. WS54-88275 A or in Zeitschrift far Naturforschung 1976, 328-337 and 338-345, and also indirect (two-step) synthesis via acetonin (2,2,4,4,6-pentamethyl-1,2,5,6-tetrahydropyrimidine), for example described in DE 24 29 935 A1 or DE 24 29 936 A1, or via phorone (2,6-dimethyl-2,5-heptadien-4-one), for example described in DE 2 352 127 A1. In the two-step TAA synthesis via acetonin, acetonin is firstly formed from acetone and ammonia, and then further reacts in a subsequent step, with elimination of one equivalent of ammonia, to give TAA. In the case of the synthesis process via acetonin, however, while both species (TAA and acetonin) are always formed simultaneously, acetonin formation is nonetheless greatly kinetically favoured over TAA formation. In the "single-step" TAA synthesis, acetonin is merely not isolated.

The preparation of TAA is in principle equally possible whether catalysed homogeneously (mainly by ammonium salts) or heterogeneously (e.g. on acidic ion exchangers).

Most documents from the prior art relate to homogeneously catalysed reactions. Most commonly mentioned in this case are calcium chloride (e.g. in Chemical Industries 2003, 89, 559-564; Zeitschrift for Naturforschung 1976, 328-337 and 338-345), ammonium chloride (e.g. in JP 2003-206277 A; JP 2001-31651 A; JPH4-154762 A) and hydrazine derivatives (e.g. in JPS54-88275 A, JPS54-112873 A). However, problems arise when using these catalysts. For instance, the use of calcium chloride has the disadvantage of a very slow reaction taking place. In the case of ammonium chloride, the reaction rate is higher but the chloride used exhibits high corrosiveness with respect to steel. Hydrazine derivatives, on the other hand, exhibit very high toxicity.

Besides these, reactions on heterogeneous catalysts have also been described, for example in CN108 383 704 A. EP 3 663 284 A1, DE 28 07 172 A1 and CN 103224465 A.

TAA is generally prepared in a matrix in which the acetone is present in a large excess and serves as both reaction partner and solvent. Therefore, at the end of the reaction there results a crude product which, in addition to TAA, contains a large proportion of acetone, unreacted ammonia, water formed by the condensation, and also, in homogeneously catalysed processes, the catalyst. In addition, further secondary components are also present, for example acyclic condensation products (e.g. diacetone alcohol, diacetonamine, mesityl oxide, phorone, etc.), cyclic condensation products [e.g. acetonin, 2,2,4,6-tetramethyl-2,3-dihydropyridine (hereinafter "TMDH-pyridine")] or higher molecular weight condensation products ("high boilers").

Some acyclic addition and condensation products (e.g. diacetone alcohol [4-hydroxy-4-methylpentan-2-one], diacetonamine [4-amino-4-methylpentan-2-one], mesityl oxide [4-methylpent-3-en-2-one], phorone, etc.) may, for their part, be reacted instead of acetone as reactants with ammonia to give TAA, which is utilized for example in processes including an internal recycling stream.

Such a process-internal recycling stream is described for example in DE 28 07 172 A1. As described in examples 5a and 6a of DE 28 07 172 A1, to this end the individual components of the TAA crude product are separated by distillation and the reactive components acetone and mesityl oxide are then reused as reactant.

For this, the crude product from the TAA synthesis is heated, and the individual components are removed, respectively condensed and recycled back. This involves a high energy expenditure and also leads to losses of acetone which have to be compensated for by adding fresh acetone to the system.

There was therefore a need for an efficient process for synthesizing TAA which does not have the aforementioned problems and which in particular enables a simple, energy-extensive and hence efficient reutilization of the acetone which has not reacted during the TAA reaction.

A process which achieves this object has now surprisingly been found.

SUMMARY OF THE INVENTION

It has surprisingly been found that a particularly efficient process fir preparing TAA is made possible by feeding the excess acetone, removed from the crude product of the TAA preparation, together with fresh acetone back into the process. To this end, the acetone is removed from the crude product and absorbed in gaseous form in countercurrent into the fresh acetone. This process avoids complex removal steps, in particular the energy-intensive condensation of acetone, and thus enables reutilization of excess acetone with a lower energy expenditure compared to conventional processes.

Accordingly, the process according to the invention is a, preferably continuous, process for preparing triacetonamine, comprising the following steps:

(a) reaction of an acetone stream $S_{Ac1}$ and an ammonia stream $S_{Am1}$ in the presence of a catalyst K1 to give a crude product stream $S_{RP1}$ comprising triacetonamine, acetone, (b) at least partial distillative removal of acetone from $S_{RP1}$ to obtain a gaseous stream $S_{Ac2}$ comprising acetone, (c) at least partial absorption of the gaseous stream $S_{Ac2}$ in countercurrent into a liquid acetone stream $S_{Ac3}$ to obtain a liquid acetone stream $S_{Ac4}$, (d) repetition of step (a), with the acetone stream $S_{Ac4}$ being used as the acetone stream $S_{Ac1}$.

The invention also includes the following embodiments:

1. Process for preparing triacetonamine, comprising the following steps:
   (a) reaction of an acetone stream $S_{Ac1}$ and an ammonia stream $S_{Am1}$ in the presence of a catalyst K1 to give a crude product stream $S_{RP1}$ comprising triacetonamine, acetone,
   (b) at least partial distillative removal of acetone from $S_{RP1}$ to obtain a gaseous stream $S_{Ac2}$ comprising acetone,
   (c) at least partial absorption of the gaseous stream $S_{Ac2}$ in countercurrent into a liquid acetone stream $S_{Ac3}$ to obtain a liquid acetone stream $S_{Ac4}$,
   (d) repetition of step (a), with the acetone stream $S_{Ac4}$ being used as the acetone stream $S_{Ac1}$.

2. Process according to Embodiment 1, wherein the at least partial distillative removal of acetone from $S_{RP1}$ which takes place in step (b) is performed in a distillation column.

3. Process according to Embodiment 1 or 2, wherein the temperature range used in the distillation in step (b) is below the boiling point of triacetonamine.

4. Process according to any of Embodiments 1 to 3, wherein, prior to and/or during the distillative removal of the acetone from crude product stream $S_{RP1}$ as per step (b), water is added to crude product stream $S_{RP1}$ and at least one of the by-products in crude product stream $S_{RP1}$, selected from the group consisting of phorone diacetone alcohol, diacetonamine, acetonin, and isophorone, is at least partially reacted with water so that at least one of the by-products in crude product stream $S_{RP1}$ is at least partially cleaved into acetone.

5. Process according to any of Embodiments 1 to 4, wherein step (a) is carried out at a temperature of 20° C. to 180° C.

6. Process according to any of Embodiments 1 to 5, wherein the molar ratio of acetone used in step (a) to ammonia used in step (a) is 3:1 to 20:1.

7. Process according to any of Embodiments 1 to 6, wherein K1 is a heterogeneous catalyst.

8. Process according to any of Embodiments 1 to 7, wherein in step (c) a portion of the acetone in the gaseous stream $S_{Ac2}$ obtained in step (b) is absorbed into the liquid acetone stream $S_{Ac3}$ and the remaining portion is condensed.

9. Process according to any of Embodiments 1 to 8, wherein said process is performed continuously.

DETAILED DESCRIPTION OF THE INVENTION

1. Step (a)

In step (a) of the process according to the invention, an acetone stream $S_{Ac1}$ and an ammonia stream $S_{Am1}$ are reacted in the presence of a catalyst K1 to give a crude product stream $S_{RP1}$ comprising triacetonamine, acetone.

A crude product stream $S_{RP1}$ comprising triacetonamine, acetone is obtained in the process. This therefore also comprises, in addition to the desired product TAA, unreacted acetone. The crude product stream $S_{RP1}$ possibly also comprises unreacted ammonia and by-products. A possible by-product is in particular mesityl oxide. Mesityl oxide is the simplest condensation product which is always formed, at least in small amounts, in the reaction of ammonia and acetone to give TAA by aldol condensation of two molecules of acetone. Higher molecular weight condensation products of acetone with itself or ammonia are also formed in the reaction in step (a) and are accordingly included in particular in the crude product stream $S_{RP1}$. These are predominantly by-products selected from the group consisting of diacetone alcohol, diacetonamine, acetonin, phorone, and isophorone, preferably selected from the group consisting of diacetone alcohol, diacetonamine, acetonin and isophorone.

The reaction in step (a), like the entire process of the invention, is preferably carried out continuously.

In continuous operation, all chemicals are preferably metered in simultaneously at the reaction temperature. In continuous operation, any reactor known to those skilled in the art can be used, for example a continuous flow tube, a continuous stirred tank, a stirred tank cascade, and also possible combinations of these individual elements. In this case, preference is given to using a combination of one or more reactors with internal or external circuit, followed by a postreactor with flow tube characteristics.

The reaction time in step (a) in continuous operation is given by the overall residence time of the reactants in the reactor and is in the range from 1 to 15 hours, preferably in the range from 3 to 9 hours, particularly preferably in the range from 5 to 7 hours.

The "volume space velocity" for ammonia in continuous operation is, in step (a), in particular 0.01 to 124.20 $h^{-1}$, preferably 0.03 to 5.25 $h^{-1}$, most preferably 0.06 $h^{-1}$ (this corresponds to the volume of ammonia flowing through this reactor per hour and per volume of the reactor, abbreviated to "LHSV").

The "volume space velocity" for acetone in continuous operation is, in step (a), in particular 0.15 to 1.33 $h^{-1}$, preferably 0.66 to 1.17 $h^{-1}$ (this corresponds to the volume of acetone flowing through this reactor per hour and per volume of the reactor).

The reaction in step (a) can take place in the presence of further solvents or just in acetone, i.e. without the addition of further solvents. In cases in which a solvent is used in step (a), all solvents which do not impede the reaction can be used. In particular, the possible solvents are aliphatic solvents, preferably pentane, hexane, heptane, octane, decane, cyclohexane, tetramethylsilane; aromatic solvents, preferably benzene, toluene, xylene; ether compounds, preferably diethyl ether, dipropyl ether, dibutyl ether, methyl tert-butyl ether; halogenated solvents, preferably dichloromethane, chloroform, tetrachloromethane; alcohols, preferably methanol, ethanol, propanol, isopropanol, butanol, cert-butanol; esters, preferably methyl acetate, ethyl acetate, propyl acetate, butyl acetate. Particularly preferably, the reaction in step (a) takes place in acetone without the addition of further solvents.

The reaction in step (a) is preferably carried out at elevated temperature, in particular at temperatures in the range from 20° C. to 180° C. preferably in the range from 40° C. to 100° C., more preferably in the range from 55° C. to 90° C., even more preferably in the range from 60° C. to 90° C., most preferably at 75° C.

The reaction in step (a) is in particular carried out either at the autogenous pressure of the components or at elevated pressure. Thus, the reaction in step (a) is preferably carried out at a pressure in the range from 1 to 16 bar, more preferably at a pressure in the range from 1 to 15 bar, even more preferably at a pressure in the range from 7 to 14 bar, even more preferably still at 12 bar.

Ammonia is preferably metered in as pure substance, i.e. as gas, in step (a) of the process according to the invention, and is present in particular during the reaction dissolved in acetone or dissolved in the reaction mixture.

Acetone is preferably metered in as pure substance in step (a). Alternatively, preference is given to using acetone which has been removed in step (b) in a previously executed round of the process according to the invention and is recycled as described in step (c).

In addition, it is possible for not just acetone and ammonia but also condensation products of the acetone with itself or ammonia to be present in the acetone stream $S_{Ac1}$ in step (a). These condensation products may originate from previous steps of reaction of ammonia and acetone to give TAA.

Step (a) of the process according to the invention is carded out in the presence of a catalyst K1. Usable catalysts K1 are all catalysts mentioned in the prior art for this type of reaction. The catalyst K1 here can be homogeneous or heterogeneous, but is preferably heterogeneous.

Suitable homogeneous catalysts K1 are all homogeneous catalysts described in the prior art for this type of reaction, for example Bronsted acids, salts of these acids or Lewis acids, as described in EP 2 706 056 A1.

The term "Bronsted acids" in the context of the invention includes in particular hydrochloric acid, sulfuric acid, nitric acid, organic acids (RCOOH) or sulfonic acids (RSO$_3$H), with R being selected from the group consisting of saturated, unsaturated, branched, unbranched, ring-closed, open-chain aliphatic, aromatic, substituted or unsubstituted hydrocarbon radicals. Substituted hydrocarbon radicals in the context of the invention are hydrocarbon radicals substituted with heteroatoms, especially hydrocarbon radicals substituted with one or more —OH, —NH, —CN, alkoxy and/or halogen radicals, preferably substituted with one or more halogen radicals, particularly preferably substituted with one or more radicals selected from F, Cl, Br and I, very particularly preferably substituted with one or more radicals selected from F and Cl.

"Salts of a Bronsted acid" in the context of the invention are in particular ammonium salts (i.e. salts with ammonia, amines, hydrazines, hydroxylamines) or phosphonium salts (i.e. salts with phosphanes). Lewis acids in the context of the invention are in particular compounds from the 4th or 13th group of the periodic table, preferably halides (AlCl$_3$, BF$_3$, TiCl$_4$), alkoxides [Al(OR*)$_3$, B(OR*)$_3$, Ti(OR*)$_4$] or alkyl compounds (e.g. AlR*$_3$), with R* being selected from the group consisting of saturated, unsaturated, branched, unbranched, ring-closed, open-chain aliphatic, aromatic, substituted or unsubstituted hydrocarbon radicals.

Lewis acids in the context of the invention are also salts of Lewis-acidic alkali metals or alkaline earth metals (e.g. CaCl$_2$, MgCl$_2$, LiCl).

Preference is given, in cases in which K1 is a homogeneous catalyst, to said catalyst being selected from the group of ammonium salts, especially from the group comprising salts of ammonia and strong Bronsted acids [e.g. hydrochloric acid, sulfuric acid, nitric acid, organic acids (RCOOH) or sulfonic acids (RSO$_3$H), with R** being selected from the group consisting of saturated, unsaturated, branched, unbranched, ring-closed, open-chain aliphatic, aromatic, substituted or unsubstituted hydrocarbon radicals].

Preference is given, in cases in which K1 is a homogeneous catalyst, to said catalyst being ammonium nitrate. Ammonium nitrate has the advantage of being cheap, non-toxic, halide-free and hence less corrosive.

However, the catalyst K1 used is preferably a heterogeneous catalyst, in particular a solid acidic catalyst as described for example in DE 28 07 172 A1, CN 103224465 A or DE 10 2010 062 804 A1. These are catalysts which are practically insoluble in the reaction medium. For this purpose, preference is given to using a catalyst which is inorganic or organic and has active acid groups, preferably sulfonic ester groups or phosphoric ester groups. The terms "sulfonic ester croups" and "phosphoric ester groups" respectively refer to the bonding of the sulfur or phosphorus atom to the respective support via an oxygen atom. It goes without saying that in the context of the invention a sulfonic ester group has an acidic "—OS(O)OH" group and a phosphoric ester group has an acidic "—OP(O)(OH)$_2$" group, which groups can be deprotonated to a respective "—OS(O)O$^-$" group or "—OP(O)(O$^-$)$_2$" group.

K1 is accordingly especially selected from the group consisting of aluminium hydrosilicates of bentonite and/or montmorillonite type, inorganic ion exchangers based on aluminium silicate of zeolite type, mordenite type, erionite type or also diatomaceous earth treated with phosphoric acid at 700 to 1100° C., as described in CA 772 201.

Heterogeneous catalysts that are particularly preferred for K1 are ion exchange resins, especially cation exchange resins. These are preferably acidic.

Suitable ion exchange resins for K1 include in particular those having an inorganic basis (for example silicon dioxide) or organic basis (for example polystyrene or polystyrene copolymers, such as styrene-divinylbenzene copolymers), preferably having an organic basis, and having protic acid groups, especially alkylsulfonic ester groups, sulfonic ester groups (—SO$_3^-$), phosphoric ester groups, especially sulfonic ester groups.

A particularly preferred heterogeneous catalyst for K1 is selected from the following group:
  a catalyst having a polymer resin, especially polystyrene or styrene-divinylbenzene copolymer, preferably polystyrene, and protic acids, especially —SO$_3^-$ groups, as functional groups (commercially available as Amberlyst® 15, Amberlite® 200, Lewatit® SP 120 or Lewatit® K2621); polystyrene sulfonate with the CAS number: 28210-41-5 can in addition also be used;
  a catalyst which has protic acids, especially sulfonic acids in polymeric form, and can be perfluorinated (described in DE 10 2010 062 804 A1, U.S. Pat. No. 4,831,146). This may for example be a sulfonated tetrafluoroethylene (CAS number: 31175-20-9) or a solid-supported perfluorinated sulfonic acid in polymeric form with silicon dioxide as the support material. Such catalysts are, inter alia, available under the trade names Nafion®, Aciplex® F, Femion®, Neosepta®, Fumion® F. A preferred catalyst is Nafion® SAC-13, Nafion® SAC-13 comprises porous silicon dioxide particles onto which Nafion® has been adsorbed with a loading of about 13% by weight;
  poly(2-acrylamido-2-methyl-1-propanesulfonic acid), marketed as PolyAMPS® from Lubrizol.

The catalyst K1 most preferably used is a heterogeneous catalyst having a polymer resin, especially polystyrene or styrene-divinylbenzene copolymer, preferably polystyrene, and protic acids, especially —SO$_3^-$ groups, as functional groups (commercially available as Amberlyst® 15, Amberlite® 200, Lewatit® SP 120 and Lewatit® K2621).

The use ratios of the reactants in step (a) of the process according to the invention can be selected within broad ranges; acetone is in particular used in excess relative to ammonia. Preferably, the molar ratio of acetone used in step (a) to ammonia used in step (a) is 3:1 to 20:1, with a ratio of 6:1 to 10:1 being preferred and a ratio of 7:1 being particularly preferred.

The amount of catalyst K1 used is not particularly restricted and can be determined by those skilled in the art. Typically, if the catalyst is a homogeneous catalyst from the group of the Bronsted acids, salts of these acids or Lewis acids, preferably an ammonium salt, even more preferably is ammonium nitrate, it can be used in a molar ratio of ammonia to catalyst, preferably ammonium nitrate, in the range from 1:0.8 to 1:0.02. Very particularly preferably, the molar ratio of acetone:ammonia:ammonium nitrate is in the range from 7 to 8:0.9 to 1.1:0.085 to 0.098.

In the preferred embodiment, in which a solid, acidic ion exchanger is used for K1, the latter can be used as a fixed bed, for example at an amount of 10% to 20% by volume based on the total amount of the acetone used in step (a) and—if such was used—of the mesityl oxide.

Following step (a) of the process according to the invention, a crude product stream $S_{RP1}$ is then obtained which, in addition to the desired product triacetonamine, also comprises the originally used reactant acetone, and also possibly ammonia and possibly mesityl oxide as by-product and possibly at least one by-product selected from the group consisting of diacetone alcohol, diacetonamine, acetonin, phorone, and isophorone, preferably selected from the group consisting of diacetone alcohol, diacetonamine, acetonin, phorone, and isophorone.

The proportion of the TAA, acetone, mesityl oxide, water and the stated by-products in RP1 is not further restricted and results from the stoichiometry and the specific reaction conditions. The proportion of each respective compound can be determined by GC. For example, after the reaction there is a mixture containing a content of acetone of 55% to 60% by weight, of mesityl oxide of 10% by weight, of TMDH-pyridine of 5% to 6% by weight, of the sum of diacetonamine, diacetone alcohol and phorone of 4% to 6% by weight, of TAA of 14% to 16% by weight, and of components boiling higher than TAA (for example isophorone) of 3% to 4% by weight, and the proportion of water is 7% by weight.

2. Step (b)

In step (b) of the process according to the invention, acetone is at least partially removed from $S_{RP1}$. This is carried out by distillation, preferably in a distillation column.

This produces a gaseous stream $S_{Ac2}$ comprising acetone. $S_{Ac2}$ possibly also comprises ammonia and/or mesityl oxide. If the crude product stream $S_{RP1}$ comprises ammonia, $S_{Ac2}$ preferably also comprises ammonia.

Removal of the catalyst K1 also optionally takes place during or before, preferably before, step (b). This may be done by addition of a base. For example, NaOH is added if K1 is an ammonium salt, and the sodium nitrate which then precipitates out is subsequently removed.

When using a heterogeneous catalyst, a separate purification step becomes superfluous or is at least significantly simpler, since for example when using a fixed bed catalyst, this catalyst remains in the reactor or in other cases can remain in the reaction tank and/or can be removed by filtration. For this reason also, the use of a heterogeneous catalyst for K1 is to be preferred.

Step (b) is in particular carried out at a pressure of 0.5 to 2 bar, preferably at standard pressure.

Step (b) is preferably carried out at a temperature which is above the boiling point of acetone and mesityl oxide but below the boiling point of the typical byproducts, which is the case when it is below the boiling point of diacetone alcohol, which is the lowest boiling of the usual by-products.

Even more preferably, step (b) is carried out at a temperature which is above the boiling point of acetone but below the boiling point of mesityl oxide (and hence also below the boiling point of diacetone alcohol, diacetonamine, TMDH-pyridine, acetonin, phorone, triacetonamine and isophorone).

The boiling points of the typical by-products diacetone alcohol (CAS number 123-42-2; boiling point at standard pressure: 166° C.), acetonin (CAS number 556-72-9; boiling point ~170° C.), diacetonamine (CAS number 625-04-7, boiling point 180° C.), phorone (CAS number 504-20-1; boiling point at standard pressure: 197° C.) are between the boiling points of acetone (CAS number 67-64-1; boiling point at standard pressure: 56° C.) or mesityl oxide (CAS number 141-79-7; boiling point at standard pressure: 130° C.) and TAA (boiling point at standard pressure: 205° C.), and in the case of isophorone (CAS number 78-59-1; boiling point at standard pressure: 215° C.) even greater than these.

Since the boiling point of ammonia is below the boiling point of acetone, it is possible in step (b) for ammonia possibly present in the crude product stream $S_{RP1}$ also to be removed along with acetone. In this embodiment, the gaseous stream $S_{Ac2}$ obtained also comprises ammonia in addition to acetone. However, this is advantageous since in the following step (c) ammonia is also absorbed into the liquid acetone stream $S_{Ac3}$ and thus less fresh ammonia needs to be led into the system.

In a preferred embodiment of the present invention, prior to and/or during the distillative removal of the acetone from crude product stream $S_{RP1}$ as per step (b), water is added to crude product stream $S_{RP1}$ and at least one of the by-products in crude product stream $S_{RP1}$, selected from the group consisting of phorone, diacetone alcohol, diacetonamine, acetonin, and isophorone, preferably selected from the group consisting of diacetone alcohol, diacetonamine, acetonin and isophorone, is at least partially reacted with water so that at least one of the by-products in crude product stream $S_{RP1}$ is at least partially cleaved into acetone. This increases the efficiency of the process according to the invention even further since more acetone which is easier to remove is therefore obtained.

Water is added to $S_{RP1}$ in the preferred embodiment before and/or during the distillative removal of acetone from $S_{RP1}$ which takes place in step (b). It goes without saying that the addition of water "before the removal of acetone from $S_{RP1}$" means that this point in time is between steps (a) and (b), since it is only after step (a) that the crude product $S_{RP1}$ is obtained.

The addition of water shifts the equilibrium from the side of the by-products to the side of the cleavage products of these same by-products, that is to say besides acetone predominantly mesityl oxide. The water resulting from the reaction in step (a) and possibly still present at least to some extent in $S_{RP1}$ is not sufficient to adequately ensure this shift of the equilibrium. It is instead necessary to add at least a certain amount of additional water to $S_{RP1}$ in order to shift the equilibrium in the following reaction to the side of the desired product acetone.

In particular, in this preferred embodiment of the process according to the invention, water is added in an amount of ≥0.1% by weight, preferably ≥0.5% by weight, more preferably ≥1% by weight, even more preferably ≥5% by weight, more preferably still in the range from 5% to 40% by weight, even more preferably still in the range from 10% to 20% by weight, based in each case on the sum total of the weights of phorone, diacetone alcohol, diacetonamine, acetonin and isophorone included in $S_{RP1}$. This proportion can be determined by those skilled in the art using gas chromatography. The total weight of $S_{RP1}$ can be determined in a continuous process by determining the flow rate (mass flow meter).

Alternatively, in this preferred embodiment of the process according to the invention, water can be added in an amount of ≥1% by weight, preferably ≥3% by weight, more preferably ≥4% by weight, even more preferably ≥5% by weight, more preferably still in the range from 5% to 40% by weight, even more preferably still in the range from 10% to 20% by weight, based in each case on the total weight of the amount of acetone used in step (a) of the process according to the invention.

The reaction of the added water in the preferred embodiment with at least one of the by-products in $S_{RP1}$ selected from the group consisting of phorone, diacetone alcohol, diacetonamine, acetonin, and isophorone, preferably selected from the group consisting of diacetone alcohol, diacetonamine, acetonin and isophorone, to give acetone can then be carried out wider the conditions familiar to those skilled in the art. This involves a hydrolysis of the by-products to acetone. The temperature range used for this purpose is in particular <205° C., preferably <204° C., is more preferably in the range from 30° C. to 200° C., is even more preferably in the range from 70° C. to 185° C.

Preferably, according to the preferred embodiment of the process according to the invention, water is added to $S_{RP1}$ while in step (b) acetone is at least partially removed from $S_{RP1}$ by distillation.

This embodiment is even more preferable when the at least partial distillative removal of acetone from $S_{RP1}$ in step (b) is performed in a distillation column.

Even more preferably still, the reaction of the added water in this preferred embodiment with at least one of the by-products in $S_{RP1}$, selected from the group consisting of phorone, diacetone alcohol, diacetonamine, acetonin, and isophorone, preferably selected from the group consisting of diacetone alcohol, diacetonamine, acetonin, and isophorone, to give acetone, is then performed in the gas phase.

In this case, the water is in particular supplied to the distillation column during the distillative removal, for example by a feed of water into the distillation column or by addition of steam to the distillation column. The reaction of at least one of the by-products diacetone alcohol, diacetonamine, acetonin, phorone, and isophorone, preferably of the by-products selected from the group consisting of diacetone alcohol, diacetonamine, acetonin and isophorone, with water to give acetone then takes place in the distillation column.

This embodiment has proved to be particularly advantageous since this embodiment ensures particularly well that the secondary components are decomposed in a controlled manner and the undesired reverse reaction of the TAA is suppressed. This is particularly well ensured, and it is accordingly preferred, when the temperature range used in the distillation in step (b) is below the boiling point of TAA, with the pressure in particular being standard pressure, preferably is <205° C. at standard pressure, more preferably is <204° C. at standard pressure, even more preferably is in the range from 30° C. to 200° C. at standard pressure, even more preferably still is in the range from 70° C. to 185° C. at standard pressure.

The removal of TAA from the distillation residue of step (b) of the process according to the invention can otherwise take place by crystallization, distillation, preferably with distillation, which even more preferably takes place in a downstream distillation column.

3. Step (c)

The invention then involves at least partially absorbing the gaseous stream $S_{Ac2}$ obtained in step (b) in countercurrent into a liquid acetone stream $S_{Ac3}$.

In the context of the invention, "at least partially" means that in step (c) either the entirety of or only a portion of the acetone in the gaseous stream $S_{Ac2}$ obtained in step (b) is absorbed in countercurrent into a liquid acetone stream $S_{Ac3}$. Preferably, in step (c) only a portion of the acetone in the gaseous stream $S_{Ac2}$ obtained in step (b) is absorbed into a liquid acetone stream $S_{Ac3}$ and the remaining portion is condensed. In this preferred embodiment, in step (c) more preferably 1% to 99% by weight, more preferably 20% to 90% by weight, even more preferably 30% to 80% by weight, even more preferably still 50% to 70% by weight, of the acetone in the gaseous stream $S_{Ac2}$ obtained in step (b) is condensed and the remainder of the acetone in the gaseous stream $S_{Ac2}$ obtained in step (b) is absorbed in countercurrent into the liquid acetone stream $S_{Ac3}$.

The acetone stream $S_{Ac3}$ is typically acetone which has to be added to the system because of the consumption in the reaction to give TAA.

In contrast to conventional processes in which acetone distilled from the crude product is condensed and then possibly supplied back to the process, this has the advantage that the recovery of the acetone is readily possible and the energy for the condensation and recycling of the acetone isolated from the crude product stream $S_{RP1}$ does not have to be applied.

Step (c) is preferably carried out in a gas scrubber (gas stripper) known to those skilled in the art.

In step (c), in particular a liquid acetone stream $S_{Ac3}$ is typically led from top to bottom while the gaseous stream $S_{Ac2}$ is led at least in part in the opposite direction and contacts the liquid acetone stream $S_{Ac3}$, so that the liquid acetone stream $S_{Ac3}$ at least partially absorbs the gaseous stream $S_{Ac2}$.

In step (c), the gaseous stream $S_{Ac2}$ preferably has a temperature which is at least 1° C. above the boiling point of the acetone at the respective pressure, therefore at standard pressure in particular in the range from 57° C. to 100° C., preferably in the range from 58° C. to 80° C., more preferably in the range from 59° C. to 70° C., even more preferably in the range from 60° C. to 65° C.

In step (c), the liquid acetone stream $S_{Ac3}$ preferably has a temperature which is at least 10° C. below the boiling point of the acetone at the respective pressure, therefore at standard pressure in particular in the range from −10° C. to 40° C. more preferably in the range from 0° C. to 30° C., more preferably in the range from 5° C. to 25° C. even more preferably in the range from 8° C. to 20° C., even more preferably in the range from 10° C. to 15° C., most preferably at 12° C.

This best guarantees that the acetone stream $S_{Ac4}$ obtained after step (c) is liquid and at the same time that the gaseous stream $S_{Ac2}$ after the distillation does not have to be cooled so greatly, which would make a higher energy expenditure necessary.

Following step (c) of the process according to the invention, a liquid acetone stream $S_{Ac4}$ is then obtained which is made up of the liquid acetone stream $S_{Ac3}$ and the acetone absorbed from the gaseous stream $S_{Ac2}$.

4. Step (d)

In step (d) of the process according to the invention, the liquid acetone stream $S_{Ac4}$ is then reacted again in a further reaction with an ammonia stream $S_{Am1}$ as described in step (a).

The following examples are intended to illustrate the invention without restricting it.

Example 1

(According to the Invention)

Two cylindrical reactors connected in series were filled with Lewatit K2621 (polystyrene catalyst with —$SO_3^-$ as functional group, from Lanxess) such that this catalyst material was arranged delimited by screens above and below. The bed volume of the catalyst was in each case 600 ml in the water-moist state. The reactor was continuously charged with 630 g/h of acetone and 25 g/h of ammonia. A temperature of 75° C. and a pressure of 14 bar were set. The feed was in total 961.83 g (16.58 mol) of acetone. The LHSV (liquid hourly space velocity, i.e. the volume of reactants added per hour, relative to the reactor volume) was 0.03 to 0.06 $h^{-1}$ for the ammonia and 0.66 to 1.33 $h^{-1}$ for the acetone.

1 kg of the reactor output was mixed with 3% to 5% by weight of water based on the amount of acetone used and subsequently worked up by distillation at standard pressure on a rectification column.

Distillation was carried out here for a time sufficient for all low boilers (acetone, mesityl oxide, diacetone alcohol, diacetonamine) to be removed; TMDH-pyridine and TAA and further high boilers formed were however removed from the bottom as waste products or products of value. Intermediate boilers such as acetonin and phorone were hydrolysed to the greatest extent possible to low-boiling components and were removable as a result.

The acetone removed in the distillation column was passed in gaseous form in countercurrent in a gas stripper with a liquid stream of fresh acetone which had a temperature of 12° C. The gaseous acetone was absorbed into the liquid acetone in the process and the liquid mixed stream obtained thereafter was introduced into the reactors for further conversion to TAA.

This procedure generated a marked reduction in the energy expenditure compared to the separate condensation of the removed acetone and mixing with additional fresh acetone.

This energy saving made possible a marked increase in efficiency of the process.

Comparative Example (Not According to the Invention, Corresponds to Example 5/5a from Laid-Open Specification DE 28 07 172 A1).

A cylindrical reactor was filled with Lewatit® SP 120 such that the catalyst material was arranged separated by screens between two layers of clay Raschig rings. The bulk volume of the catalyst was 650 ml in the moist state, but shrunk after treatment with acetone to 500 ml. The reactor was brought to 100° C. reaction temperature by electric heating and then continuously charged with 1000 ml/h of acetone and 50 ml/h of ammonia by pumping both reactants in liquid form from reservoirs into the lower reactor section. The reaction product passed in liquid form from the upper reactor section into a separator and was continuously withdrawn from the latter; the system was maintained under a pressure of 70 bar with inert gas (Hp).

The distillative workup of the crude product was performed as described on page 12 of DE 28 07 172 A1, by distillative separation of the crude product. The first three fractions comprising acetone, mesityl oxide and ammonia (as decomposition product of the diacetonamine) were used together with fresh acetone as reactant.

The composition of the obtained crude product that was established during continuous operation was as described in DE 28 07 172 A1:64.5% by weight of acetone, 4.6% by weight of mesityl oxide, 4.0% by weight of diacetonamine, 7.6% by weight of nitrogen-containing intermediate fractions, 18.8% by weight of triacetonamine and 0.5% by weight of higher-boiling compounds.

With continuous performance, a TAA yield of 69.9% was obtained by this embodiment (based on the amount of acetone used in total and conversion).

Example 2

(According to the Invention)

The procedure described in the comparative example was repeated with the following difference:

The distillate streams corresponding to the first three fractions were mixed with fresh, cooled acetone in countercurrent and then reused as reactant. When performing this process continuously, a crude product composition of 63.5% by weight of acetone, 10.4% by weight of mesityl oxide, 6.3% by weight of diacetonamine, 4.9% by weight of nitrogen-containing intermediate fractions, 13.7% by weight of triacetonamine and 1.2% of higher-boiling compounds is established.

It is therefore surprisingly found that while the TAA concentration in the crude product is lower than that in the crude product according to the comparative example, the total yield (based on the amount of acetone used in total and conversion) of TAA was increased to 73.6%.

It is assumed that the reason for this is that the crude product of example 2, compared to that of the comparative example, has a higher proportion of products such as mesityl oxide, acetone and diacetonamine, which can be reused as reactants. In addition, the proportion of nitrogen-containing intermediate fractions in the crude product according to example 2 is lower than that of the crude product obtained in the comparative example. These nitrogen-containing intermediates (i.e., higher molecular weight products such as TMDH-pyridine) cannot be used again as reactant and are accordingly lost for further reactions.

In the process according to the invention, in comparison to the processes of the prior art, in particular that of DE 28 07 172 A1 an advantageous range of by-products is accordingly obtained in the crude product. At the same time, a higher proportion of reutilizable by-products can as a result be resupplied to the reaction in a simple, energy-efficient manner. This leads to a higher TAA yield, based on the amount of acetone used in total.

The invention claimed is:

1. A process for preparing triacetonamine, the process comprising:
    (a) reacting an acetone stream $S_{Ac1}$ and an ammonia stream $S_{Am1}$ in the presence of a catalyst K1 to give a crude product stream $S_{RP1}$ comprising triacetonamine and acetone,
    (b) performing an at least partial removal by distillation of acetone from $S_{RP1}$ to obtain a gaseous stream $S_{Ac2}$ comprising acetone, (c) performing an at least partial absorption of the gaseous stream $S_{Ac2}$ in countercurrent into a liquid acetone stream $S_{Ac3}$ to obtain a liquid acetone stream $S_{Ac4}$, (d) repeating (a), wherein the acetone stream $S_{Ac4}$ is used as the acetone stream $S_{Ac1}$.

2. The process according to claim 1, wherein the at least partial removal by distillation of acetone from $S_{RP1}$ which takes place in (b) is performed in a distillation column.

3. The process according to claim 1, wherein a temperature range used in the at least partial removal by distillation in (b) is below the boiling point of triacetonamine.

4. The process according to claim 1, wherein, prior to and/or during the at least partial removal by distillation of acetone from the crude product stream $S_{RP1}$ as per (b), water is added to the crude product stream $S_{RP1}$,
wherein the crude product stream $S_{RP1}$ comprises by-products, and
wherein at least one of the by-products in the crude product stream $S_{RP1}$ selected from the group consisting of phorone, diacetone alcohol, diacetonamine, acetonin, and isophorone, is at least partially reacted with water so that at least one of the by-products in crude product stream $S_{RP1}$ is at least partially cleaved into acetone.

5. The process according to claim 1, wherein (a) is carried out at a temperature of 20° C. to 180° C.

6. The process according to claim 1, wherein a molar ratio of acetone used in (a) to ammonia used in (a) is 3:1 to 20:1.

7. The process according to claim 1, wherein the catalyst K1 is a heterogeneous catalyst.

8. The process according to claim 1, wherein in (c) a portion of the acetone in the gaseous stream $S_{Ac2}$ obtained in (b) is absorbed into the liquid acetone stream $S_{Ac3}$ and the remaining portion is condensed.

9. The process according to claim 1, wherein said process is performed continuously.

10. The process according to claim 1, wherein a reaction time in (a) is 5 to 7 hours.

11. The process according to claim 1, wherein a volume space velocity for ammonia in (a) is 0.03 to 5.25 $h^{-1}$.

12. The process according to claim 1, wherein a volume space velocity for acetone in (a) is 0.66 to 1.174 $h^{-1}$.

13. The process according to claim 1, wherein a temperature in (a) is 60 to 90° C.

14. The process according to claim 1, wherein pressure in (a) is 7 to 14 bar.

15. The process according to claim 1, wherein 1% to 99% by weight of said acetone in said gaseous stream $S_{Ac2}$ obtained in (b) is condensed and a remainder of said acetone in said gaseous stream $S_{Ac2}$ is absorbed in counter current into said liquid acetone stream $S_{Ac3}$.

16. The process according to claim 1, wherein (C) is carried out in a gas scrubber.

17. The process according to claim 1, wherein gaseous stream $S_{Ac2}$ has a temperature of form 57° C. to 100° C.

18. The process according to claim 1, wherein said liquid acetone stream $S_{Ac3}$ has a temperature which is at least 10° C. below the boiling point of said acetone at a respective pressure.

19. The process according to claim 1, wherein said liquid acetone stream $S_{Ac3}$ has a temperature in a range from 10° to 15° C.

* * * * *